United States Patent [19]

Vallee et al.

[11] Patent Number: 4,952,403

[45] Date of Patent: Aug. 28, 1990

[54] IMPLANTS FOR THE PROMOTION OF HEALING OF MENISCAL TISSUE

[75] Inventors: Bert L. Vallee, Brookline; Thomas V. King, Winchester, both of Mass.

[73] Assignee: President and Fellows of Harvard College, Boston, Mass.

[21] Appl. No.: 204,097

[22] Filed: Jun. 8, 1988

Related U.S. Application Data

[63] Continuation-in-part of Ser. No. 64,215, Jun. 19, 1987.

[51] Int. Cl.$^5$ ............................................. A61K 9/52
[52] U.S. Cl. ........................................ 424/422; 424/423; 424/424; 424/425; 424/426; 424/457; 424/460; 424/462; 424/489; 424/491; 424/497; 424/499; 424/501; 514/2; 514/8; 514/21; 514/953; 514/955; 514/963; 514/964; 604/890.1; 604/891.1
[58] Field of Search ............... 514/2, 8, 21; 604/890, 604/891; 424/422–426, 457, 460, 462, 489, 491, 497, 499, 501

[56] References Cited

U.S. PATENT DOCUMENTS

| | | | |
|---|---|---|---|
| 4,450,150 | 5/1984 | Sidman | 424/426 |
| 4,503,038 | 3/1985 | Banda et al. | 424/95 |
| 4,529,590 | 7/1985 | La Veen | 424/95 |
| 4,690,682 | 1/1987 | Lim | 424/497 |
| 4,699,788 | 10/1987 | Catsinpoolas et al. | 424/95 |
| 4,725,609 | 2/1988 | Kull et al. | 514/355 |
| 4,727,137 | 2/1988 | Vallee | 530/35 |

OTHER PUBLICATIONS

Felt et al., *Biochem.* 24, pp. 5480–5486.
Strydom et al., *Biochem.* 24, 1985, pp. 5486–5494.
Furachi et al., *Biochem.* 24, 1985, pp. 5494–5499.
Rettura et al., *FASEB* Abst. #4309, 1977.
Cabaud et al., *Am. J. Sports Med.*, 9(3), 1981, pp. 129–134.
Blackshear, *Scientific* American 1979, pp. 66–73.
King, J., Bone Joint Surg., vol. 18, pp. 333–342 (1936).
Cabaud et al., Am J. Sports Med., vol. 9(3), pp. 129–134 (1981).
Heatley, J., Bone Joint Surg., vol. 62-B, pp. 397–402 (1980).
Arnoczky et al., *Am. J. Sports Med.*, vol. 10(2), pp. 90–95 (1982).
Rettura et al., *FASEB* Abstract No. 4309, 61st Annual Meeting, Chicago (1977).

*Primary Examiner*—Garnette Draper
*Attorney, Agent, or Firm*—Allegretti & Witcoff

[57] ABSTRACT

Healing of injured avascular tissue is promoted by applying angiogenic factor in proximity to the injured tissue.

4 Claims, No Drawings

IMPLANTS FOR THE PROMOTION OF HEALING OF MENISCAL TISSUE

This application is a continuation-in-part of U.S. Ser. No. 07/064,215 filed June 19, 1987.

This invention relates to a method of promoting healing of injured normally avascular tissue and pertains more specifically to applying an angiogenic factor in proximity to the injury to promote healing.

It has long been known that normally avascular tissue, in particular fibrocartilage such as the menisci of the knee or the wrist, of the end of the clavicle, or of the temporomandibular joint is resistant to vascularization and healing except at the vascularized perimeter, after either accidental injury such as laceration or tearing or after deliberate surgical incision. King, J. Bone Joint Surg., Vol. 18, pp. 333–342 (1936) taught that a torn dog meniscus can be healed by connective tissue provided that the tear communicates with the synovial membrane laterally, a teaching that was confirmed by Cabaud et al., Am. J. Sports Med., Vol. 9(3), pp. 129–134 (1981). The latter showed that healing occurred in lacerated menisci of dogs and monkeys through vascular scar tissue contiguous with the peripheral synovial tissue and extended to the depth of the laceration. Heatley, J. Bone Joint Surg., Vol. 62-B, 397–402 (1980) demonstrated healing of incised rabbit menisci by suturing the incision and showed that invasion of synovial cells, not vascular tissue, was the prelude to healing, resulting in a scar which was not very vascular. Arnoczky et al., Am. J. Sports Med., Vol. 10(2), pp. 90–95 (1982) showed that blood vessels are found only in the peripheral quarter of the human knee meniscus and concluded that the vascular supply is too sparse to support an inflammatory response promoting spontaneous healing after laceration of the fibrocartilage.

Angiogenic factors have been known to play an important role in wound healing, Rettura et al., FASEB abstract No. 4309, 61st annual meeting, Chicago, (1977) and have been derived from tumor cells and wound fluid, Banda et al., Proc. Natl. Acad. Sci., USA, Vol. 79, pp. 7773–7777 (1982), U.S. Pat. No. 4,503,038; and from retinal cells, D'Amore, Proc. Natl. Acad. Sci., USA, Vol. 78, pp. 3068–3072 (1981). Folkman et al., J. Exp. Med., Vol. 133, pp. 275–288 (1971) isolated a tumor angiogenesis factor from the Walker 256 rat ascites tumor. The factor was mitogenic for capillary endothelial cells and was inactived by RNase. Tuan et al., Biochemistry, Vol. 12, pp. 3159–3165 (1973) found mitogenic and angiogenic activity in the nonhistone proteins of the Walker 256 tumor. The active fraction was a mixture of proteins and carbohydrate. A variety of animal and human tumors have been shown to produce angiogenesis factor(s), Phillips and Kumar, Int. J. Cancer, Vol. 23, pp. 82–88 (1979) but the chemical nature of the factor(s) was not determined. A low molecular weight non-protein component from Walker 256 tumors has also been shown to be angiogenic and mitogenic, Weiss et al., Br. J. Cancer, Vol. 40, pp. 493–496 (1979). An angiogenesis factor with a molecular weight of 400–800 daltons was purified to homogeneity by Fenselau et al., J. Biol. Chem., Vol. 256, pp. 9605–9611 (1981), but it was not further characterized. Human lung tumor cells have been shown to secrete an angiogenesis factor comprising a high molecular weight carrier and a low molecular weight, possibly non-protein, active component, Kumar et al., Int. J. Cancer, Vol. 32, pp. 461–464 (1983). Vallee et al., Experientia, Vol. 41, pp. 1–15 (1985) found angiogenic activity associated with three fractions from Walker 256 tumors. Tolbert et al., U.S. Pat. No. 4,229,531, disclosed the production of angiogenesis factor from the human adenocarcinoma cell line HT-29. Heparin-Binding Growth Factors, Transforming Growth Factor Alpha, and Transforming Growth Factor Beta are also known angiogenic factors. An angiogenic protein known as angiogenin has been isolated and characterized from human carcinoma cells, Fett et al., Biochem., Vol. 24, pp. 5480–5486 (1985) and is the material of choice for use in the present invention.

Thus the peptide of the formula

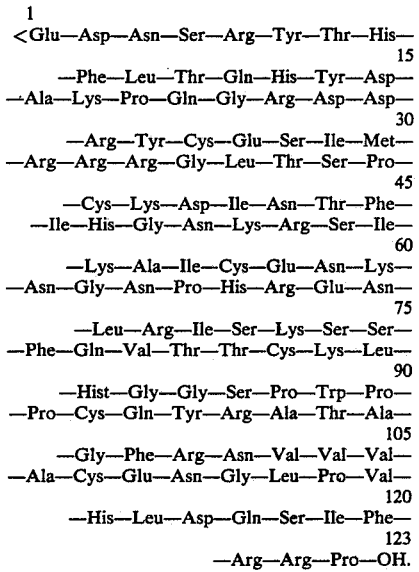

and angiogenic fragments or portions thereof or peptide derivatives thereof having one to several amino acids deleted or substituted while retaining substantially the same angiogenic activity as the peptide of the formula given above are suitable for practicing this invention. The symbol <Glu is employed to represent a pyroglutamic acid moiety.

Those skilled in the genetic engineering arts will recognize a variety of peptides related to the above peptide structure which can be conveniently made by genetic engineering techniques. Those peptides may have leader segments such as those coded for by the met initiation codon and the like. Thus a wide variety of peptides equivalent to the above structure are readily available through conventional genetic engineering techniques.

There has now been found a method of promoting healing of normally avascular tissue of a meniscus after injury or rupture such as laceration, tearing or incision which comprises providing an effective dose of angiogenic factor in proximity to said injured tissue. For best results the angiogenic factor is applied or implanted in proximity to or immediately adjacent to the injury site, preferably in direct contact with the injured tissue, for example in the form of composition comprising the angiogenic factor and a physiologically acceptable nontoxic carrier. The carrier may be liquid or solid and may, for example, be a polymer such as methyl cellulose or a copolymer of ethylene and vinyl acetate or other polymeric composition providing for slow release of the angiogenic factor over a prolonged period of time, in which latter case the angiogenic factor is in the form of a timed release implant. The method of the invention has particular application to fibrocartilage such as the menisci described above.

The dosage required for effective use varies over a broad range depending upon the identity and purity of the angiogenic factor employed. In the case of pure angiogenin, the dose may range from 500 to 900 ng for each 2 to 4 mm length of defect to be healed when administered in a carrier such as methyl cellulose from which it is released rapidly. In any specific case the optimal size of the effective dose can be determined by routine testing. Since healing is normally completed by the present method within 6 to 10 weeks, timed release implants providing a supply of angiogenic factor extending for approximately the same time period, i.e. 6 to 10 weeks, may be used.

The angiogenic factor upon implantation or administration adjacent the injury in the avascular central portion of a meniscus induces neovascularization, followed by healing of the injury, even without the use of sutures.

The following specific example is intended as an illustration of the invention and not as a limitation on its scope.

Ninety-seven male New Zealand white rabbits weighing between 5 and 7 kilograms each, housed in individual cages, were fed a standard diet except that tetracycline was added to the drinking water both before and after surgery as a prophylaxis.

The rabbits were anesthetized using an intramuscular injection of Acepromazine maleate (Tech America Group, Inc., Elwood, KS: 2-acetyl-10-(3-dimethylamino-propyl)phenothiazine hydrogen maleate) 1.5 mg/kg body weight and ketamine (Bristol Laboratories, Syracuse, N.Y.: DL-2-(o-chlorophenyl)-2(methylamino)cyclohexanone hydrochloride) 25 mg/kg body weight, and a local subcutaneous injection of 2 cc of 1% xylocaine (Astra Pharmaceutical Products, Inc., Westborough, Mass.: acetamide, 2-(diethylamino)-N-(2,6-dimethylphenyl)-monohydrochloride). The entire right lower extremity was shaved, prepped with 70% alcohol solution and draped with sterile towels. The knee joint was exposed through a lateral parapatellar skin and retinacular incision The patella was luxated medially, the origin of the peroneal tendon was divided and the knee was flexed. Under a binocular dissecting microscope using 10x power, a micro skin hook was placed into the anterior horn of the meniscus. The meniscus was pulled anteriorly, and the anterior third of the lateral meniscus was visualized. A small scalpel was used to cleave an approximately 0.8 mm by 2.5 mm horizontal pocket into the body of the meniscus starting 2 mm from the meniscal rim. The pocket was extended posteriorly just under the visible surface of the tissue within the middle third of the meniscal body. Care was taken to minimize trauma to the synovium.

Methyl cellulose (4000 Cp) was autoclaved and then dissolved (1% w/v) in sterile water by stirring overnight at 4° C. Lyophilized, salt-free samples of angiogenin were suspended by gentle stirring in 1% methyl cellulose for 2 hrs. at 4° C. Ten-microliter volumes were placed on a clean, dry mylar sheet and air-dried under laminar flow conditions to form a clear pellet or disc 3 mm. in diameter, each containing 100 ng of angiogenin. The sheet containing the pellets was placed in a sterile square Petri dish, placed in a desiccator, and lyophilized for a further 60 min. to ensure that the pellets were completely dry. Control methyl cellulose discs were prepared containing no angiogenin. Under sterile conditions, the discs were individually removed from the plastic sheet with forceps, folded and each separately inserted into the sharp end of a 20 gauge needle.

The sharp tip of the 20 gauge needle holding the sample was inserted into the pocket of the meniscus of each rabbit and an obturator from a 20 gauge spinal needle was used to eject the disc from the needle, deliver the sample accurately, and impact the sample into the meniscal tissue. A 1 mm vertical knife cut was then made medial to the pocket to simulate a longitudinal laceration.

The knee was extended, the patella reduced, and the tissues were irrigated with 0.9% saline solution containing 500 mg Gentamicin per liter. The retinaculum was closed with interrupted figure of eight sutures of 3-0 Vicryl absorbable suture and the skin was closed with a running subcuticular suture of 4-0 Vicryl. The rabbits were permitted to run freely in their cages and were fed a standard diet. Tetracycline was added to their drinking water pre- and post-operatively.

Groups of rabbits were sacrificed at intervals of 3, 6, 8, 9, 12, and 26 weeks using a lethal intravenous injection of Acepromazine maleate 3 mg/kg and Ketamine 50 mg/kg. The knee joint was examined grossly using the dissecting microscope and findings were recorded. The observer was blinded to the identity of the sample implanted. Results were graded according to the presence or absence of neovascularization. For those samples graded positively for neovascularization, a second observation regarding the presence or absence of the pocket and knife cut ("healing") was recorded.

Samples for histologic examination were stored in 10% neutral buffered formalin solution. Transverse sections through the meniscus and underlying bone were decalcified, embedded and stained with hematoxylin and eosin for light microscopy.

Neovascularization was observed in 39 of 75 (52%) menisci that had been implanted with angiogenin. Neovascularization was characterized as a pannus of connective tissue with prominent blood vessels growing from the contiguous synovium over the anterior horn and body of the meniscus in the direction of the implantation pocket. Closure ("healing") of the pocket introitus and knife cut occurred in eight of these 39 (21%) neovascularized menisci. "Healing" appeared to be secondary to a connective tissue pannus formation that was vigorous enough to overgrow the pocket and obliterate the introitus. Narrowing of the anterior horn of the meniscus often accompanied this vigorous response as though some healing contraction of "scar tissue" had occurred.

The angiogenin knees with no neovascularization were clearly devoid of any post-operative change and appeared as they had on the day of implantation with no pannus or blood vessel formation. The pocket and knife cut were unchanged and no methyl cellulose was found.

In the control group, 20 of 22 (91%) knees appeared exactly as they had on the day of surgery with no neovascularization and no change in the pocket or knife cut. In two knees (9%) a pannus of connective tissue was found growing over the anterior horn toward the pocket and knife cut. No prominent blood vessels were visible and the connective tissue did not reach the pocket or knife cut. Nevertheless, these were graded as positive findings.

The statistical difference between the angiogenin and control groups was significant.

In the angiogenin group, neovascularization was seen in 27% (three of eight) of those sacrificed before four weeks, in 57% (30 of 53) in those between six and ten weeks and in 43% (6 of 14) of those after ten weeks. An analysis of the healing times is shown in Table 1.

In the control group, the two "positive" responses were seen at six weeks and eight weeks.

TABLE 1

Angiogenin Implantation and Time Elapsed to Harvest

| # of weeks elapsed | # rabbits | # positive results | |
|---|---|---|---|
| 3 | 8 | 3 | (27%) |
| 6 | 14 | 5 | (35%) |
| 8 | 23 | 12 | (52%) |
| 9 | 16 | 13 | (81%) |
| 12 | 8 | 4 | (50%) |
| 26 | 6 | 2 | (33%) |

Histologic sections stained with hematoxylin and eosin demonstrated capacious vascular channels surrounded by a loose fibroblastic tissue invading the meniscal fibrocartilage from the periphery. Synovial tissue with prominent vessels was adherent to the surface of the meniscus. In addition, an unusual histologic picture with what appeared to be new chondrocytes was identified at the interface between the invading tissue and the normal fibrocartilage.

Similar results were obtained using ethylene:vinyl acetate copolymer (60:40) together with rabbit albumin as the carrier for angiogenin.

Optimization of Rabbit Albumin Content of Elvax Spheres

A series of pellets incoporating various amounts of rabbit albumin and the copolymer (Elvax 40P) were prepared in order to determine the optimum ratio of copolymer to albumin for release of incorporated angiogenin. Rabbit serum albumin, 50 mg, and the desired amount of [$^{125}$I] labelled angiogenin were dissolved in 1 mL of water and sterilized by filtration through a 0.22 micron filter into a sterile tube. The sterile solution was then frozen and lyophilized. The rabbit albumin serves as a bulk carrier and an effector of angiogenin release, and being of rabbit origin it should not produce any immunological reaction after implantation into rabbits. The lyophilized albuminangiogenin solid was mixed under sterile conditions to yield a homogeneous powder. The uniformity of particle size is important to the effectiveness of the preparation. Then 1 mL of 10% solution of copolymer in dichloromethane (100 mg copolymer) was added to the tube containing the desired amount of powder, the tube sealed and the contents stirred on a vortex mixer at high speed for up to 10 minutes to produce a uniform suspension This suspension was drawn up into a 5 mL disposable syringe fitted with an 18 gauge steel needle. The suspension was then extruded through the needle drop by drop into 20 mL of absolute ethanol in a 50 mL beaker cooled to −78° C. in a dry ice/ethanol bath. The drops gelled on contact with the cold ethanol into spherical shapes which sank to the bottom of the beaker. After 10 minutes the beaker was removed from the cold bath and allowed to warm to room temperature. The beads turned white as the dichloromethane was slowly extracted into the ethanol. After an overnight incubation in a fresh ethanol solution, the pellets were air dried in a laminar flow hood. The pellets (approximately 50 in number) produced in this manner were about 1 mm$^3$ in size. The rate of release of angiogenin from these pellets was measured by incubating them in physiological saline at 37° C. and the release of [$^{125}$I] angiogenin with time was measured. Pellets containing 0 and 10% albumin by weight released a small percent of angiogenin on day 1 and none thereafter. Presumably the material released was on the surface of the pellets. Pellets containing 40 and 50% albumin by weight released a large percent of the angiogenin on day 1 (58 and 77% respectively) while the 30% albumin pellets showed the desired moderate release rates. From this information a practical composition consisting of two parts by weight of copolymer and one of rabbit albumin was used to prepare pellets containing from 10 nanograms to 10 micrograms of angiogenin per pellet.

The effectiveness of such pellets was tested by following essentially the surgical procedure described above by using in place of the methyl cellulose pellets as the implant in the meniscal pocket, pyramidal-shaped pieces cut from pellets of 2:1 copolymer:albumin; one or two pieces containing a total of 100 ng angiogenin were placed in each pocket using forceps. Controls did not contain angiogenin. A single 4/0 vicryl or 6/0 proline suture on a P-3 needle was typically used to close the pocket. Animals were harvested at 8 weeks and the menisci examined for healing and neovascularization.

The results were as shown in Table 2 below:

TABLE 2

| | No. rabbits | | | Percentage showing Positive Effect |
|---|---|---|---|---|
| | Healed | Neovascularization | No effect | |
| Angiogenin | 21 | 21 | 45 | 48 |
| Control | 2 | 0 | 10 | 17 |

Blends or mixtures of albumin with other polymers may also be used as carriers for angiogenin in timed release implants. In each case, the proportions for optimum effectiveness can be determined by a simple test.

What is claimed is:

1. An implant for promoting healing of normally avascular tissue of a meniscus after injury which comprises a physiologically acceptable solid carrier which contains and releases for a period of at least about three weeks a vascularizing amount of an angiogenic polypeptide of the formula:

```
        1
<Glu—Asp—Asn—Ser—Arg—Tyr—Thr—His—
                                         15
     —Phe—Leu—Thr—Gln—His—Tyr—Asp—
  —Ala—Lys—Pro—Gln—Gly—Arg—Asp—Asp—
                                         30
        —Arg—Tyr—Cys—Glu—Ser—Ile—Met—
    —Arg—Arg—Arg—Gly—Leu—Thr—Ser—Pro—
                                         45
        —Cys—Lys—Asp—Ile—Asn—Thr—Phe—
     —Ile—His—Gly—Asn—Lys—Arg—Ser—Ile—
                                         60
        —Lys—Ala—Ile—Cys—Glu—Asn—Lys—
     —Asn—Gly—Asn—Pro—His—Arg—Glu—Asn—
                                         75
        —Leu—Arg—Ile—Ser—Lys—Ser—Ser—
     —Phe—Gln—Val—Thr—Thr—Cys—Lys—Leu—
                                         90
        —Hist—Gly—Gly—Ser—Pro—Trp—Pro—
     —Pro—Cys—Gln—Tyr—Arg—Ala—Thr—Ala—
                                         105
        —Gly—Phe—Arg—Asn—Val—Val—Val—
     —Ala—Cys—Glu—Asn—Gly—Leu—Pro—Val—
                                         120
```

```
—His—Leu—Asp—Gln—Ser—Ile—Phe—
                                      123
              —Arg—Arg—Pro—OH.
``` or polypeptides having substantially the same amino acid sequence and angiogenic activity.

2. An implant according to claim 1, wherein the physiologically acceptable solid carrier is a blend of a solid polymer and albumin.

3. An implant according to claim 2, wherein the solid polymer is ethylene: vinyl acetate copolymer.

4. An implant according to claim 3, wherein the period of time is about 6 to 10 weeks.

* * * * *